United States Patent
Sun et al.

[11] Patent Number: 5,861,019
[45] Date of Patent: Jan. 19, 1999

[54] IMPLANTABLE MEDICAL DEVICE MICROSTRIP TELEMETRY ANTENNA

[75] Inventors: Weimin Sun, Plymouth; Gregory J. Haubrich, Champlin; Garry L. Dublin, Maple Grove, all of Minn.

[73] Assignee: Medtronic Inc., Minneapolis, Minn.

[21] Appl. No.: 900,624

[22] Filed: Jul. 25, 1997

[51] Int. Cl.⁶ .................................................. H04B 1/38
[52] U.S. Cl. .............................................. 607/60; 607/36
[58] Field of Search ................................ 607/60, 30, 32, 607/36

[56] References Cited

U.S. PATENT DOCUMENTS

| | | | |
|---|---|---|---|
| 4,681,111 | 7/1987 | Silvian | 128/419 PT |
| 4,785,827 | 11/1988 | Fischer | 128/783 |
| 4,991,582 | 2/1991 | Byers et al. | 129/419 P |
| 5,057,106 | 10/1991 | Kasevich et al. | 607/122 |
| 5,058,581 | 10/1991 | Silvian | 128/419 PG |
| 5,117,825 | 6/1992 | Grevious | 128/419 PG |
| 5,127,404 | 7/1992 | Wyborny et al. | 128/418 PG |
| 5,168,871 | 12/1992 | Grevious | 128/419 PG |
| 5,292,343 | 3/1994 | Blanchette et al. | 607/32 |
| 5,324,315 | 6/1994 | Grevious | 607/60 |
| 5,342,408 | 8/1994 | deCoriolis et al. | 607/32 |
| 5,354,319 | 10/1994 | Wyborny et al. | 607/32 |
| 5,470,345 | 11/1995 | Hassler et al. | 607/36 |
| 5,562,713 | 10/1996 | Silvian | 607/32 |
| 5,562,714 | 10/1996 | Grevious | 607/3 |
| 5,720,770 | 2/1998 | Nappholz et al. | 607/60 |

*Primary Examiner*—William E. Kamm
*Assistant Examiner*—Kennedy J. Schaetzle
*Attorney, Agent, or Firm*—Thomas F. Woods; Harold R. Patton

[57] ABSTRACT

A microstrip RF telemetry antenna is formed on or within the exterior surface of an implantable medical device housing that is formed either of a conductive metal or of a non-conductive dielectric material. The microstrip antenna is formed of an electrically conductive radiator patch layer that is laminated upon an exterior facing side of a dielectric substrate layer of relatively constant thickness. A conductive ground plane layer is formed on the opposite side of the dielectric substrate layer to extend parallel to and at least coextensively with the radiator patch layer. The radiator patch layer is coupled to the transceiver circuitry within the implantable medical device housing by a feedthrough extending through the dielectric substrate layer, the ground plane layer and the implantable medical device housing side wall. If the implantable medical device housing is conductive it may form the ground plane layer over which the dielectric substrate layer and the radiator patch layer are formed through deposition or other techniques. If the implantable medical device housing is formed of a suitable non-conductive dielectric material, the ground plane layer is formed on an interior surface thereof and the radiator patch layer is formed on an exterior housing surface thereof, preferably by deposition techniques. The ground plane layer may be recessed to form a cavity backed ground plane that receives the dielectric layer and radiator patch layer within the cavity. The exterior surfaces of the radiator patch layer, the dielectric layer and any exposed surface of the ground plane layer may be electrically insulated by a radome layer.

22 Claims, 10 Drawing Sheets

IMPLANTABLE MEDICAL DEVICE MICROSTRIP TELEMETRY ANTENNA

CROSS-REFERENCE TO RELATED APPLICATIONS

Reference is hereby made to commonly assigned, co-pending U.S. patent application Ser. Nos. 08/584,851 filed Jan. 11, 1996, for ADAPTIVE PERFORMANCE-OPTIMIZING COMMUNICATION SYSTEM FOR COMMUNICATING WITH AN IMPLANTED MEDICAL DEVICE in the names of S. Goedeke et al.; 08/768,605 filed Dec. 18, 1996, for IMPLANTABLE DEVICE TELEMETRY HIGH DATA TRANSMISSION RATE TELEMETRY TRANSMISSION FORMAT FOR IMPLANTED MEDICAL DEVICE in the names of J. Grevious et al.; 08/842,581 filed Mar. 4, 1997, for HIGH DATA TRANSMISSION RATE TELEMETRY TRANSMISSION FORMAT FOR IMPLANTED MEDICAL DEVICE in the names of J. Grevious et al.; and 08/813,963 filed Mar. 3, 1997, for METHOD AND APPARATUS FOR IMPLANTABLE MEDICAL DEVICE TELEMETRY in the names of J. Grevious et al.

FIELD OF THE INVENTION

The present invention relates generally to an improved telemetry antenna for an implantable medical device for use in uplink and downlink telemetry transmission between an implanted medical device and an external device programmer.

BACKGROUND OF THE INVENTION

Early implantable medical devices such as implantable cardiac pacemakers were designed to operate in a typically single operating mode governed by fixed operating parameters without any ability to change the operating mode or otherwise communicate percutaneously with external equipment. In time, it became apparent that it would be clinically desirable to vary certain of the operating parameters and/or modes of operation. An initial approach employed with implanted cardiac pacemakers involved use of miniature rheostats that could be directly accessed by a needle-like tool inserted through the patient's skin to adjust a resistance in the pacing rate or pulse width setting circuit. Later, miniaturized reed switches were incorporated into the pacing rate or pulse width circuits that responded to magnetic fields applied through the skin by an external magnet placed over the implant site. The pulse width, pacing rate and a limited number of pacing modes could be adjusted in this manner.

It was also realized that the operation of an implantable cardiac pacemaker could be observed, for example, by use of a standard ECG machine and timing of intervals between pacing pulse spikes in the ECG tracing recorded from skin electrodes on the patient. Later, it became known that this technique could be used to detect data sent from the implanted cardiac pacemaker by modulating the pacing pulse amplitude and/or width or the pacing rate. This approach could only provide a low bandpass data channel, of course, to avoid interfering with the primary function of pacing the patient's heart when necessary. One use of this technique was to monitor impending battery depletion through observation of a change in the pacing rate from a preset or programmed pacing rate in response to a battery voltage drop.

As digital circuit technology advanced, it was recognized that control of operating modes and parameters of implanted medical devices could be realized in digital or binary circuits employing memorized control states or operating parameter values. In order to change an operating mode or parameter value, "programmers" were developed based on radio frequency (RF) downlink data communication from an external programmer transceiver to a telemetry transceiver and memory incorporated within the pacemaker implantable pulse generator (IPG).

It also became possible to provide uplink data telemetry to transmit the contents of a register or memory within the IPG to the telemetry receiver within the programmer employing the same RF transmission capabilities. Today, both analog and digital data can be transmitted by uplink RF telemetry from the implanted device to the external programmer. The analog data has typically included battery voltage, sampled intracardiac electrocardiogram amplitude values, sensor output signals, pacing pulse amplitude, energy, and pulse width, and pacing lead impedance. The digital data typically includes, statistics related to performance, event markers, current values of programmable parameters, implant data, and patient and IPG identifier codes. Similar analog and digital data is telemetered from implanted cardiac monitors, drug dispensers, nerve stimulators, cardioverter/defibrillators, pacemaker/cardioverter/defibrillators, etc.

The telemetry transmission system that evolved into current common use relies upon the generation of low amplitude magnetic fields by current oscillating in an LC circuit of an RF telemetry antenna in a transmitting mode and the sensing of currents induced a closely spaced RF telemetry antenna in a receiving mode. Short duration bursts of the carrier frequency are transmitted in a variety of telemetry transmission formats. In the MEDTRONIC® product line, the RF carrier frequency is set at 175 kHz and the RF telemetry antenna of the implantable medical device is typically coiled wire wound about a ferrite core that is located within the hermetically sealed enclosure. The hermetically sealed enclosure also typically contains a battery power source and circuitry for controlling the operation of the medical device.

In an uplink telemetry transmission from an implanted medical device, it is desirable to limit the current drain from the implanted battery as much as possible simply to prolong device longevity. However, as device operating and monitoring capabilities multiply, it is desirable to be able to transmit out ever increasing volumes of data in real time or in as short a transmission time as possible with high reliability and immunity to spurious noise. As a result of these considerations, many RF telemetry transmission data encoding schemes have been proposed or currently are used that attempt to increase the data transmission rate.

An extensive description of the historical development of uplink and downlink telemetry transmission formats and is set forth in the above-referenced '851 and '963 applications and in the following series of commonly assigned patents all of which are incorporated herein by reference in their entireties. Commonly assigned U.S. Pat. No. 5,127,404 to Grevious et al. sets forth an improved method of frame based, pulse position modulated (PPM) of data particularly for uplink telemetry. The frame-based PPM telemetry format increases bandwidth well above simple PIM or pulse width modulation (PWM) binary bit stream transmissions and thereby conserves energy of the implanted medical device. Commonly assigned U.S. Pat. No. 5,168,871 to Grevious et al. sets forth an improvement in the telemetry system of the '404 patent for detecting uplink telemetry RF pulse bursts that are corrupted in a noisy environment. Commonly assigned U.S. Pat. No. 5,292,343 to Blanchette et al. sets forth a further improvement in the telemetry system of the '404 patent employing a hand shake protocol for maintaining the communications link between the external programmer and the implanted medical device despite instability in holding the programmer RF head steady during the transmission. Commonly assigned U.S. Pat. No. 5,324,315 to Grevious sets forth an improvement in the uplink telemetry system of the '404 patent for providing feedback to the programmer to aid in optimally positioning the programmer RF head over the implanted medical device. Commonly assigned U.S. Pat. No. 5,117,825 to Grevious sets forth an further improvement in the programmer RF head for regulating the output level of the magnetic H field of the RF head telemetry antenna using a signal induced in a sense coil in a feedback loop to control gain of an amplifier driving the RF head telemetry antenna. Commonly assigned U.S. Pat. No. 5,562,714 to Grevious sets forth a further solution to the regulation of the output level of the magnetic H field generated by the RF head telemetry antenna using the sense coil current to directly load the H field. Commonly assigned U.S. Pat. No. 5,354,319 to Wybomey et al. sets forth a number of further improvements in the frame based telemetry system of the '404 patent. Many of these improvements are incorporated into MEDTRONIC® Model 9760, 9766 and 9790 programmers. These improvements and the improvements described in the above-referenced pending patent applications are directed in general to increasing the data transmission rate, decreasing current consumption of the battery power source of the implantable medical device, and increasing reliability of uplink and downlink telemetry transmissions.

The current MEDTRONIC® telemetry system employing the 175 kHz carrier frequency limits the upper data transfer rate, depending on bandwidth and the prevailing signal-to-noise ratio. Using a ferrite core, wire coil, RF telemetry antenna results in: (1) a very low radiation efficiency because of feed impedance mismatch and ohmic losses; 2) a radiation intensity attenuated proportionally to at least the fourth power of distance (in contrast to other radiation systems which have radiation intensity attenuated proportionally to square of distance); and 3) good noise immunity because of the required close distance between and coupling of the receiver and transmitter RF telemetry antenna fields.

These characteristics require that the implantable medical device be implanted just under the patient's skin and preferably oriented with the RF telemetry antenna closest to the patient's skin. To ensure that the data transfer is reliable, it is necessary for the patient to remain still and for the medical professional to steadily hold the RF programmer head against the patient's skin over the implanted medical device for the duration of the transmission. If the telemetry transmission takes a relatively long number of seconds, there is a chance that the programmer head will not be held steady. If the uplink telemetry transmission link is interrupted by a gross movement, it is necessary to restart and repeat the uplink telemetry transmission. Many of the above-incorporated, commonly assigned, patents address these problems.

The ferrite core, wire coil, RF telemetry antenna is not bio-compatible, and therefore it must be placed inside the medical device hermetically sealed housing. The typically conductive medical device housing adversely attenuates the radiated RF field and limits the data transfer distance between the programmer head and the implanted medical device RF telemetry antennas to a few inches.

In U.S. Pat. Nos. 4,785,827 to Fischer, 4,991,582 to Byers et al., and commonly assigned 5,470,345 to Hassler et al. (all incorporated herein by reference in their entireties), the metal can typically used as the hermetically sealed housing of the implantable medical device is replaced by a hermetically sealed ceramic container. The wire coil antenna is still placed inside the container, but the magnetic H field is less attenuated. It is still necessary to maintain the implanted medical device and the external programming head in relatively close proximity to ensure that the H field coupling is maintained between the respective RF telemetry antennas.

Attempts have been made to replace the ferrite core, wire coil, RF telemetry antenna in the implantable medical device with an antenna that can be located outside the hermetically sealed enclosure. For example, a relatively large air core RF telemetry antenna has been embedded into the thermoplastic header material of the MEDTRONIC® Prometheus programmable IPG. It is also suggested that the RF telemetry antenna may be located in the IPG header in U.S. Pat. No. 5,342,408. The header area and volume is relatively limited, and body fluid may infiltrate the header material and the RF telemetry antenna.

In U.S. Pat. Nos. 5,058,581 and 5,562,713 to Silvian, incorporated herein by reference in their entireties, it is proposed that the elongated wire conductor of one or more medical lead extending away from the implanted medical device be employed as an RF telemetry antenna. In the particular examples, the medical lead is a cardiac lead particularly used to deliver energy to the heart generated by a pulse generator circuit and to conduct electrical heart signals to a sense amplifier. A modest increase in the data transmission rate to about 8 Kb/s is alleged in the '581 and '713 patents using an RF frequency of 10–300 MHz. In these cases, the conductor wire of the medical lead can operate as a far field radiator to a more remotely located programmer RF telemetry antenna. Consequently, it is not necessary to maintain a close spacing between the programmer RF telemetry antenna and the implanted cardiac lead antenna or for the patient to stay as still as possible during the telemetry transmission.

However, using the medical lead conductor as the RF telemetry antenna has several disadvantages. The radiating field is maintained by current flowing in the lead conductor, and the use of the medical lead conductor during the RF telemetry transmission may conflict with sensing and stimulation operations. RF radiation losses are high because the human body medium is lossy at higher RF frequencies. The elongated lead wire RF telemetry antenna has directional radiation nulls that depend on the direction that the medical lead extends, which varies from patient to patient. These considerations both contribute to the requirement that uplink telemetry transmission energy be set artificially high to ensure that the radiated RF energy during the RF uplink telemetry can be detected at the programmer RF telemetry antenna. Moreover, not all implantable medical devices have lead conductor wires extending from the device.

A further U.S. Pat. No. 4,681,111 to Silvian, incorporated herein by reference in its entirety, suggests the use of a stub antenna associated with the header as the implantable medical device RF telemetry antenna for high carrier frequencies of up to 200 MHz and employing phase shift keying (PSK) modulation. The elimination of the need for a VCO and a bit rate on the order of 2–5% of the carrier frequency or 3.3–10 times the conventional bit rate are alleged.

At present, a wide variety of implanted medical devices are commercially released or proposed for clinical implantation. Such medical devices include implantable cardiac pacemakers as well as implantable cardioverter-defibrillators, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. As the technology advances, implantable medical devices become ever more complex in possible programmable operating modes, menus of available operating parameters, and capabilities of monitoring increasing varieties of physiologic conditions and electrical signals which place ever increasing demands on the programming system.

It remains desirable to minimize the time spent in uplink telemetry and downlink transmissions both to reduce the likelihood that the telemetry link may be broken and to reduce current consumption.

Moreover, it is desirable to eliminate the need to hold the programmer RF telemetry antenna still and in proximity with the implantable medical device RF telemetry antenna for the duration of the telemetry transmission. As will become apparent from the following, the present invention satisfies these needs.

SUMMARY OF THE INVENTION

It is therefore an object of the present invention to satisfy these needs and overcome the deficiencies of the prior art implantable medical device RF telemetry antennas.

The present invention employs a microstrip antenna as the implantable medical device RF telemetry antenna and may employ a microstrip antenna as the programmer RF telemetry antenna. With respect to the implantable medical device RF telemetry antenna, a microstrip patch antenna is preferably employed that is conformal with the exterior housing of the implantable medical device. In relatively miniaturized implantable medical devices, the header assembly need not be enlarged nor its volume used to contain the RF telemetry antenna. The disadvantages of employing lead conductors, if present, are avoided. Such microstrip patch antennas operate with enhanced data bit rates and low error rates over a long distance from the external device RF telemetry antenna and provide a number of other advantages. In use, the implantable medical device microstrip patch antenna minimizes power consumption during uplink and downlink telemetry transmissions and provides near hemispheric coverage.

The implantable medical device microstrip patch antenna advantageously extends over the available surface area of the hermetically sealed enclosure housing and is conformable with its geometry. The microstrip patch antenna materials are inexpensive and bio-compatible, and fabrication costs of the housing and the attachment with the internally disposed transceiver are low. The microstrip patch antenna layers can be incorporated in a variety of forms as part of a major housing wall that can be fabricated using automated manufacturing processes.

In accordance with the present invention, the microstrip RF telemetry antenna is formed on or within the exterior housing surface of an implantable medical device housing that is formed either of a conductive metal or of a non-conductive, dielectric material. The microstrip RF telemetry antenna is formed of an electrically conductive, radiator patch layer that is laminated upon one side of a dielectric substrate layer of relatively constant thickness. A conductive, ground plane layer is formed on the opposite side of the dielectric substrate layer to extend in parallel to and at least coextensively with the radiator patch layer. The radiator patch layer is coupled to the transceiver circuitry within the implantable medical device housing by a feedthrough extending through the dielectric substrate layer and ground plane layer and the implantable medical device housing side wall.

If the implantable medical device housing is conductive, it forms the ground plane layer over which the dielectric substrate layer and the radiator patch layer are formed through deposition or other techniques. Preferably, the medical device housing is formed with an exterior surface housing recess having a housing recess depth within which the thicknesses of the dielectric substrate layer and the radiator patch layer are received. This housing recess makes the microstrip patch antenna structure conformal with the exterior contour of the housing surface and compensates for an otherwise truncated ground plane layer. By use of this recess, the ground plane layer is effectively extended into a ground plane layer extension that is substantially co-planar with and surrounding the periphery of the patch radiator layer, and the recess provides a cavity backed ground plane for the patch radiator layer.

If the implantable medical device housing is formed of a suitable non-conductive, dielectric material, the ground plane layer is formed on an interior surface thereof, and the radiator patch layer is formed on an exterior housing surface thereof preferably by electro-deposition or other techniques. An insulating layer electrically insulates the interiorly disposed ground plane layer from circuitry included within the implantable medical device housing except for a ground or reference connection therewith. Moreover, it is contemplated that at least the radiator patch layer be disposed between layers of dielectric material forming an implantable medical device housing. In this variation, a radome is formed of the exterior dielectric layer of the medical device housing, and the electrical connection of the radiator patch layer with the feedthrough pin is isolated from body fluids and tissue.

In any such configuration, the dielectric substrate layer, the radiator patch layer and the ground plane layer are conformal with the relatively planar major surfaces and any curvature of the implantable medical device housing. In the embodiments where the radiator patch layer would otherwise be exposed to body fluids, a radome formed of a layer of dielectric material overlying the radiator patch layer is preferably employed.

In the case where implantable medical device housing is non-conductive and relatively limited in surface area, compensation is preferably effected for the limited area available for forming a ground plane layer. The compensation involves forming a ground plane layer extension in the same plane as, and surrounding the periphery of, the patch radiator layer, i.e., forming a cavity backed ground plane comparable to the recess formed in the conductive housing embodiment.

Similar techniques and configurations may be employed in the fabrication of an external RF telemetry antenna for use by the external programmer for providing uplink and downlink telemetry therebetween.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

A preferred embodiment of the present invention relates to forming the improved microstrip RF telemetry antenna on or within and/or as part of the housing of an implantable medical device of the types described above. The microstrip RF telemetry antenna is preferably used with a transceiver to program or interrogate an implantable medical device memory or to uplink telemeter real time or stored data. The following description is directed to various preferred embodiments of the invention implemented in the housing of a cardiac pacemaker or pacemaker-cardioverter-defibrillator IPG and an external programmer for use therewith. However, those of skill in the art will be readily able to adapt the teachings found herein to the other implantable medical devices listed above and others to be devised. Moreover, in the description and claims, it will be understood that the term "programmer" refers to an external medical device for controlling downlink and/or uplink telemetry transmissions with the implantable medical device and may simply interrogate or otherwise receive uplink telemetry transmissions from the implantable medical device.

Figure 1:
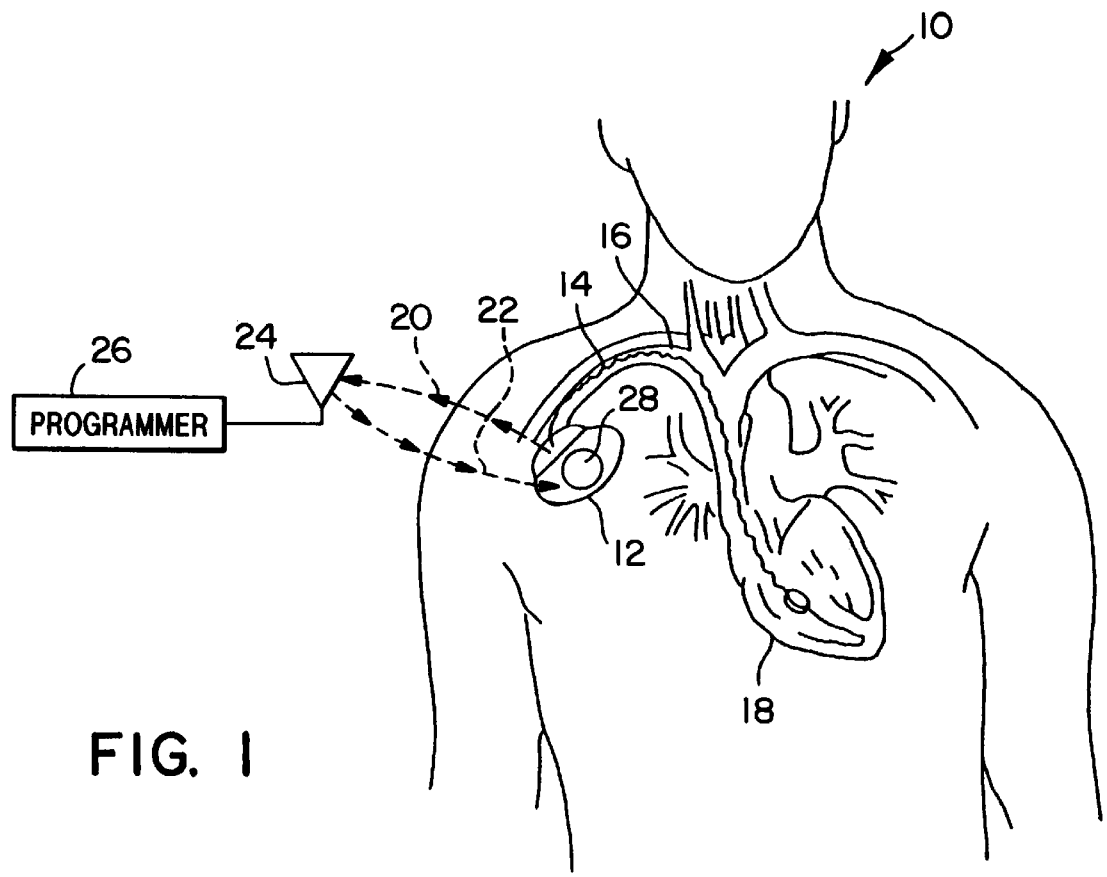
FIG. 1 is a simplified schematic view of an implantable medical device and an external programmer employing the improved RF telemetry antenna of the present invention.

FIG. 1 is a simplified schematic diagram of bi-directional telemetry communication between an external programmer 26 and an implanted medical device, e.g., a cardiac pacemaker IPG 12, in accordance with the present invention. The IPG 12 is implanted in the patient 10 beneath the patient's skin or muscle and is typically oriented to the skin surface in the manner illustrated in the above-incorporated '714 patent. IPG 12 is electrically coupled to the heart 18 of the patient 10 through pace/sense electrodes and lead conductor (s) of at least one cardiac pacing lead 14 in a manner known in the art. The IPG 12 contains an operating system that may employ a microcomputer or a digital state machine for timing sensing and pacing functions in accordance with a programmed operating mode. The IPG 12 also contains sense amplifiers for detecting cardiac signals, patient activity sensors or other physiologic sensors for sensing the need for cardiac output, and pulse generating output circuits for delivering pacing pulses to at least one heart chamber of the heart 18 under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to device operating history or sensed physiologic parameters for telemetry out on receipt of a retrieval or interrogation instruction. Such an IPG 12 is described in detail in the above-referenced '581 application, incorporated by reference herein. All of these functions and operations are well known in the art, and many are employed in other programmable, implantable medical devices to store operating commands and data for controlling device operation and for later retrieval to diagnose device function or patient condition.

Programming commands or data are transmitted between an IPG RF telemetry antenna 28 within or on a surface of the IPG 12 and an external RF telemetry antenna 24 associated with the external programmer 26. In this case, it is not necessary that the external RF telemetry antenna 24 be contained in a programmer RF head of the type described in the above-referenced '963 application so that it can be located close to the patient's skin overlying the IPG 12. Instead, the external RF telemetry antenna 24 can be located on the case of the external programmer some distance away from the patient 10. For example, the external programmer 26 and external RF telemetry antenna 24 may be on a stand a few meters or so away from the patient 10. Moreover, the patient may be active and could be exercising on a treadmill or the like during an uplink telemetry interrogation of real time ECG or physiologic parameters. The programmer 26 may also be designed to universally program existing IPGs that employ the conventional ferrite core, wire coil, RF telemetry antenna of the prior art and therefore also have a conventional programmer RF head and associated software for selective use with such IPGs.

In an uplink telemetry transmission 20, the external RF telemetry antenna 24 operates as a telemetry receiver antenna, and the IPG RF telemetry antenna 28 operates as a telemetry transmitter antenna. Conversely, in a downlink telemetry transmission 30, the external RF telemetry antenna 24 operates as a telemetry transmitter antenna, and the IPG RF telemetry antenna 28 operates as a telemetry receiver antenna.

Figure 2:
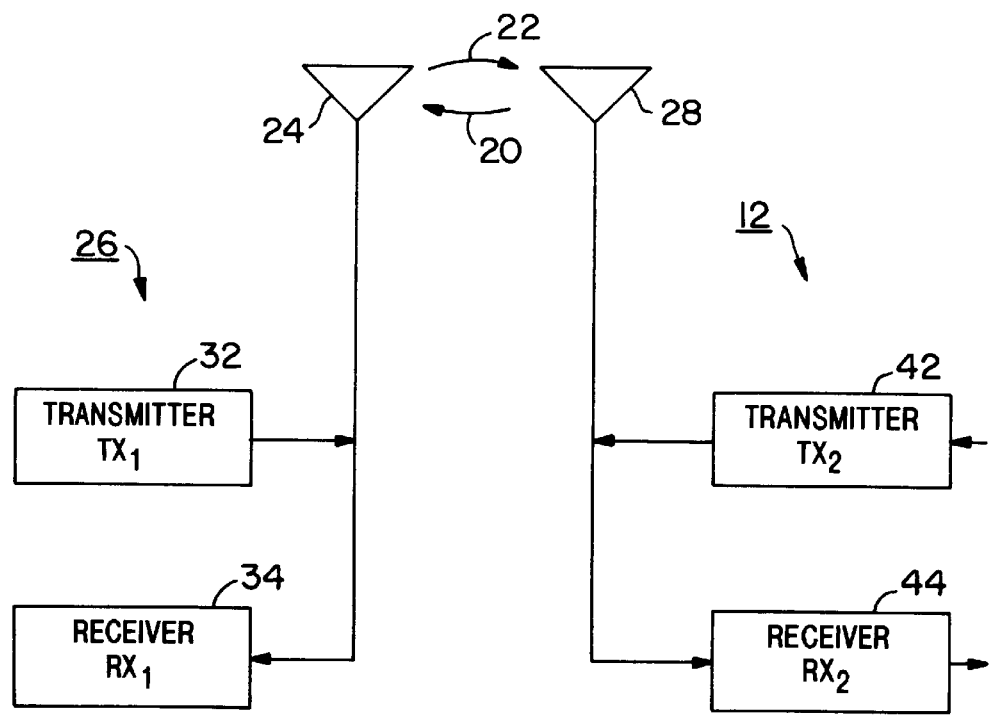
FIG. 2 is a simplified circuit block diagram of major functional uplink and downlink telemetry transmission functions of the external programmer and implantable medical device of FIG. 1.

Turning to FIG. 2, it is a simplified circuit block diagram of major functional telemetry transmission blocks of the external programmer 26 and IPG 12 of FIG. 1. The external RF telemetry antenna 24 within the programmer 26 is coupled to a telemetry transceiver comprising a telemetry transmitter 32 and telemetry receiver 34. The telemetry transmitter 32 and telemetry receiver 34 are coupled to control circuitry and registers operated under the control of a microcomputer and software as described in the above-incorporated, commonly assigned, patents and pending applications. Similarly, within the IPG 12, the IPG RF telemetry antenna 28 is coupled to a telemetry transceiver comprising a telemetry transmitter 42 and telemetry receiver 44. The telemetry transmitter 42 and telemetry receiver 44 are coupled to control circuitry and registers operated under the control of a microcomputer and software as described in the above-incorporated, commonly assigned, patents and pending applications.

In an uplink telemetry transmission 20, the telemetered data may be encoded in any of the telemetry formats described in detail in the above-incorporated patents and in the above-referenced pending '851 and '963 patent applications. In a particular example described below, the data encoding or modulation is in the form of frequency shift key (FSK) or differential phase shift key (DPSK) modulation of the carrier frequency, for example. To initiate a uplink telemetry transmission 20, the telemetry transmitter 32 in external programmer 26 is enabled in response to a user initiated INTERROGATE command to generate an INTERROGATE command in a downlink telemetry transmission 22. The INTERROGATE command is received and demodulated in receiver 44 and applied to an input of the implantable medical device central processing unit (CPU), e.g. a microcomputer (not shown). The implantable medical device microcomputer responds by generating an appropriate uplink data signal that is applied to the transmitter 42 to generate the encoded uplink telemetry signal 20. Any of the above described data encoding and transmission formats may be employed.

In the above-referenced MEDTRONIC® programmers and implantable medical devices, the frame-based telemetry format is not currently employed for downlink telemetry transmissions 22. Instead, a simpler bit stream format is employed that can be used to robustly transmit INTERROGATE commands or PROGRAM instructions under the control of a programmer CPU. Each RF pulse of the INTERROGATE instruction or command that is transmitted in the downlink telemetry transmission 22 causes the IPG antenna receiver 44 to ring. The train of induced voltages is detected and decoded by the receiver 44. After the INTERROGATE command or instruction is decoded, the stored data to be uplink transmitted is encoded into PPM modulated RF pulses in data frames, for example. The methods and apparatus for formatting such uplink data frames for MEDTRONIC® IPGs and other implantable medical devices are set forth in detail in the above-incorporated '404, '319 and '343 patents and the '851 and '963 applications. The IPG transmitter 42 applies voltage to the IPG RF antenna 28 to generate the uplink RF pulses which are transmitted through the patient's body and the intervening air to the external RF telemetry antenna 24. The transmitted signals are detected in the telemetry receiver 34 and applied as a pulse train to further decoding circuitry to decode the transmitted data so that at the data can be recorded or displayed as described above.

As illustrated in FIGS. 13–19 and described in greater detail below, at least the IPG telemetry antenna 28 of the present invention is a microstrip RF telemetry antenna. In the following description, the implantable RF telemetry antenna 28 of the present invention may be alternatively referred to as a microstrip antenna or a patch antenna or the like.

The microstrip RF telemetry antenna is formed on or within the exterior surface of the IPG housing that is formed either of a conductive metal or of a non-conductive, dielectric material. The microstrip antenna is formed of an electrically conductive, radiator patch layer that is laminated upon one side of a dielectric substrate layer of relatively constant thickness. A conductive, ground plane layer is formed on the opposite side of the dielectric substrate layer to extend in parallel with the radiator patch layer. The radiator patch layer is coupled to the transceiver circuitry within the implantable medical device housing by a feedthrough extending through the dielectric substrate layer and ground plane layer and the implantable medical device housing side wall. If the implantable medical device housing is conductive, it forms the ground plane layer over which the dielectric substrate layer and the radiator patch layer are formed through deposition or other techniques. If the implantable medical device housing is formed of a suitable non-conductive, dielectric material having a suitable dielectric constant, the ground plane layer is formed on an interior surface thereof and the radiator patch layer is formed on an exterior housing surface thereof preferably by electrodeposition techniques. An insulating layer may be used to electrically insulate the interiorly disposed ground plane layer from circuitry included within the implantable medical device housing except for a ground or reference connection therewith.

In such embodiments, it is desirable that a radome layer be formed overlying the exposed outer surface of the radiator patch layer. The radome layer ensures that the patch radiator and its electrical connection with the feedthrough pin are isolated from body fluids and tissue. In the case where the implantable medical device is formed of a non-conductive, dielectric, material, it is contemplated that at least the radiator patch layer be embedded within the implantable medical device housing. The outer layer of the dielectric housing material thereby provides a radome layer. In any such combination, the dielectric substrate layer, the radiator patch layer, the ground plane layer and the radome layer are "conformal" with any plane surface and any curvature of the implantable medical device housing.

The microstrip antenna layers can be deposited on or embedded into the exterior surface of an IPG hermetically sealed can or housing. Since any RF antenna of this type is a resonant RF radiator, the geometric size of the radiator patch layer is proportional to a half of the radiation wavelength (inversely proportional to radiation frequency).

Conversely, the desired operating frequency establishes the physical size of the radiator patch layer.

Current IPG hermetically sealed housings or cans for cardiac pacemakers typically have relatively planar opposed surfaces joined together at rounded edges so that the major planar surfaces have a diameter of about 1.5 to 2.0 inches. The IPG RF radiator patch layer can therefore be about 1.0–1.5 inches in diameter, and the ground plane is made to be somewhat greater in diameter or area. As noted below, the spatial limitations imposed on the ground plane are compensated by forming a housing recess in the major surface of the medical device housing. The housing recess extends inward of the exterior housing surface to a predetermined housing recess depth in the predetermined substrate area of the exterior housing surface for receiving the dielectric substrate therein.

The conformal microstrip antenna so formed has an inherent resonant frequency when energized. When the IPG RF telemetry antenna 28 formed in this manner is implanted in the human thoracic region, the operating frequency is scaled by the square root of the dielectric constant of the dielectric substrate of the microstrip antenna. This dielectric constant scaling factor is in the range of 7 to 9 (or more, depending on the substrate), yielding an operating frequency range of about 400 to 800 MHz. An additional scale factor of 1.5 to 2.5 may be achieved using extra pin loading.

Figure 3:
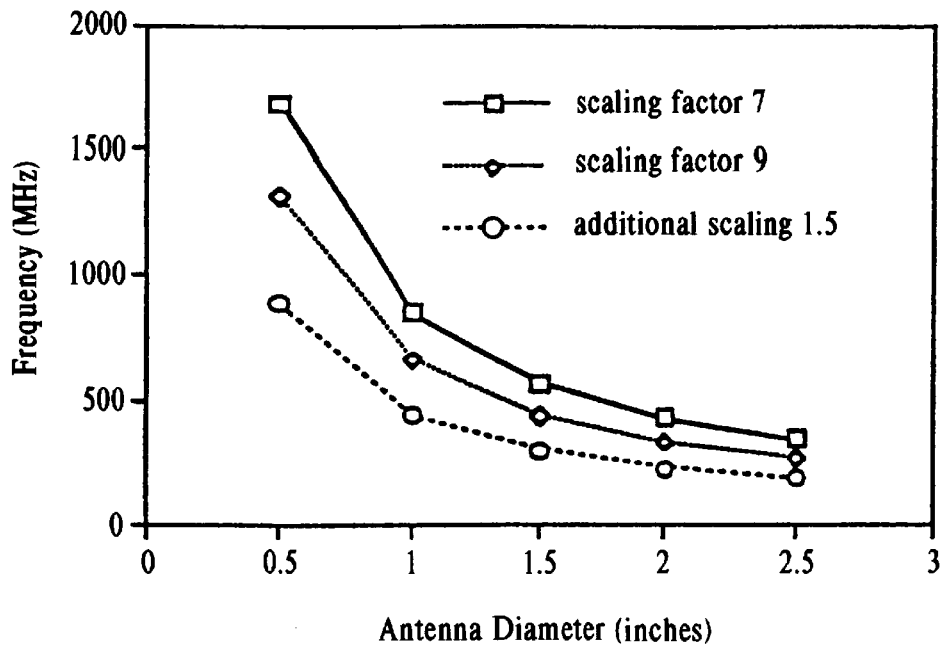
FIG. 3 is a graph depicting an exemplary relation between RF telemetry frequency and the diameter of a circular, microstrip patch antenna formed on or within the hermetically sealed housing of an implantable medical device.

FIG. 3 is a graph depicting the relation between RF telemetry frequency and the diameter of a circular microstrip patch antenna formed on or within the housing of an implantable medical device hermetically sealed enclosure taking these scaling factors into account. An implantable RF telemetry antenna with a patch diameter in the range of 1.5–1.0 inches can operate at a frequency in the range of 200–800 MHz, respectively, depending on the scaling factors.

In general, if a telemetry system has a larger bandwidth, a faster data rate can be achieved. A minimum data rate of 500 Kb/s is desirable which is well above what the ferrite core, wire coil, RF telemetry antenna located within the hermetically sealed metal enclosure can provide. Briefly a data rate is proportional to system bandwidth $$R=kB$$

where R is the bit rate, B is the bandwidth and factor k is in the range of 1 to 2. Factor k is dependent upon the modulation type used in the transceiver hardware. Therefore, if a data bit transmission rate of 500 Kb/s is desired, the minimum system frequency bandwidth must be 250–500 KHz.

Figure 4:
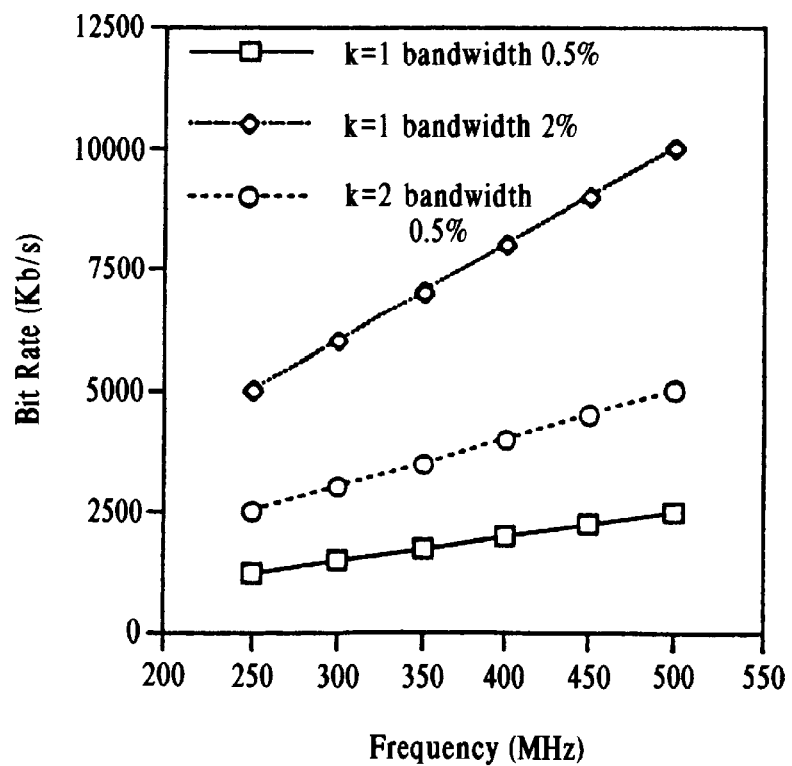
FIG. 4 is a graph depicting an exemplary relation between maximum data rate and RF telemetry frequency at differing bandwidth factors.

A microstrip patch antenna normally can provide a relative bandwidth B of 0.5%–5.0%. FIG. 4 is a graph depicting the relation between data bit rate and RF telemetry frequency at differing bandwidths B and factors k. When the operating frequency is in the range of 250–500 MHz and the bandwidth B is only 0.5% at k=1, the minimum data rate still will be about 1250 Kb/s. This bit rate is still well above current RF telemetry capabilities and requirements for uplink and downlink telemetry transmissions between an external programmer and implantable medical devices of the types listed above.

The specified bit rate defines the time frame within which a data set can be transferred from an IPG RF telemetry antenna to an external RF telemetry antenna. In clinical applications, both data transfer speed and data transfer error rate are of great importance. A lower data transfer error rate implies better data reliability and fewer occasions where the telemetry data transfer operation must be repeated. However, a lower data transfer error rate requires a higher S/N ratio which in turn requires increased radiation power. Increased radiated power emitted in uplink telemetry from an implantable medical device, e.g. IPG 12 in FIGS. 1 and 2, requires an undesirable increase in the current drain from the battery.

Figure 5:
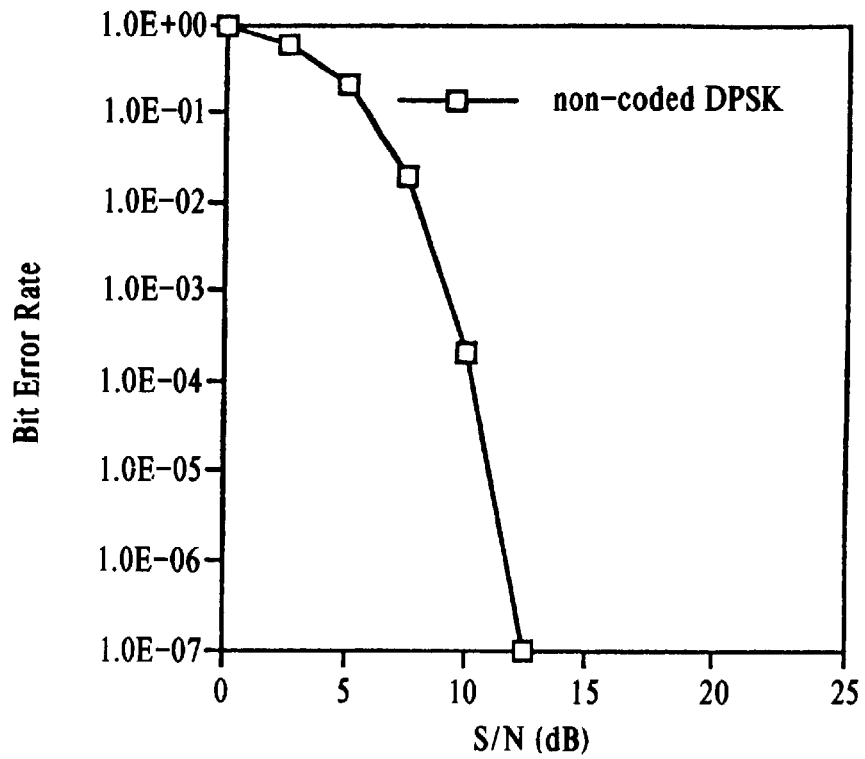
FIG. 5 is a graph depicting an exemplary relation between bit error rate and signal-to-noise (S/N) ratio employing non-coded differential phase shift key (DPSK) data encoding.

FIG. 5 is a graph depicting the relation between bit error rate and S/N ratio employing non-coded DPSK data encoding. It can be observed in FIG. 5 that a bit error rate of $10^{-5}$ normally requires a S/N ratio of 10–12 dB. By using other coding techniques, the same bit error rate can be achieved with smaller S/N ratio. Usually, the non-coded, data bit transfer error rate is used as the upper bound for the power consumption estimate.

Power efficiency is another important criterion for an implantable telemetry system because of the limited battery energy in the implantable medical device. Both body loss and distance between the IPG and external RF telemetry antennas are critical factors affecting the IPG battery power consumption during an uplink telemetry transmission. In the microstrip patch antenna designs of the present invention, the distance between the RF telemetry antennas is not the primary factor. The body loss and the system bandwidth are the primary factors establishing minimal radiated power from the implantable medical device RF telemetry antenna. The radiation power in decibel milliWatts required to deliver data at a distance (d) with a system bandwidth of 1 MHz can be expressed simply by $$P(dBm)=-114-10\ log((\lambda/4\ \pi d^2)-G_t-G_r+L_b+S/N$$

where $\lambda$ is the wavelength, d is the data link distance, $G_t$ is the patch antenna gain, $G_r$ the receiver antenna gain, $L_b$ is the body loss, and S/N is the signal-to-noise ratio required to achieve a bit error rate.

Figure 7:
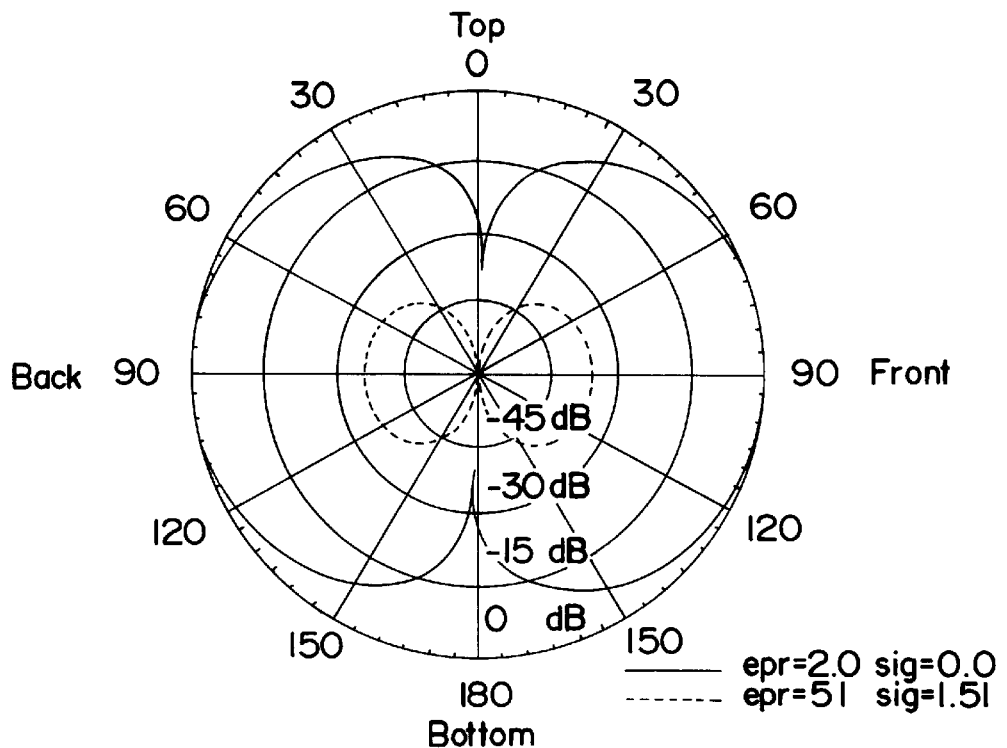
FIGS. 7 and 8 are depictions of exemplary pitch and yaw plane radiation patterns in air and in tissue.
Figure 8:
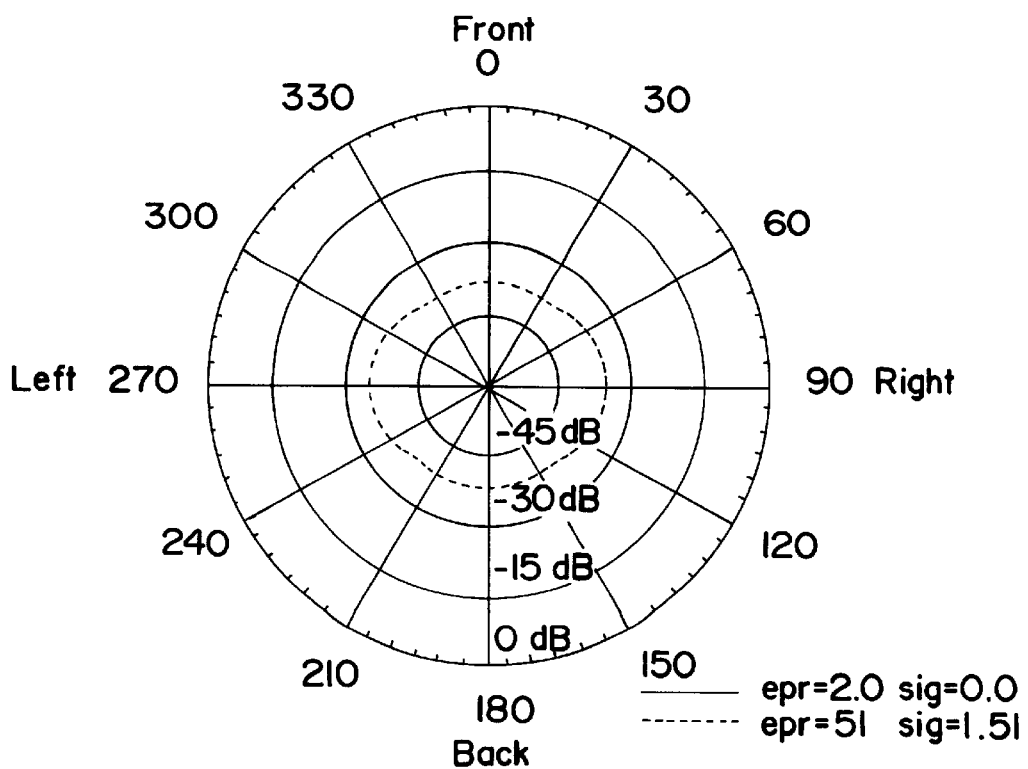

In order to estimate the power required, the body loss should be estimated first. A numerical simulation has been performed to predict the energy loss of a wave radiated by an implanted dipole antenna through the human thorax. In this simulation, assuming that the wave has to penetrate through an 8 cm thick muscle and tissue mass and the dipole antenna is operated at 350 MHz (which is the middle frequency of expected frequency range of 200–500 MHz), the body loss compared to loss-less radiation is around 35 dB. In such a case, FIGS. 7 and 8 depict pitch plane and yaw radiation patterns in air (solid lines) and in tissue (broken lines). The pitch plane of FIG. 7 is the human sagittal plane, and the yaw plane of FIG. 8 is the plane transverse to the sagittal plane.

Figure 6:
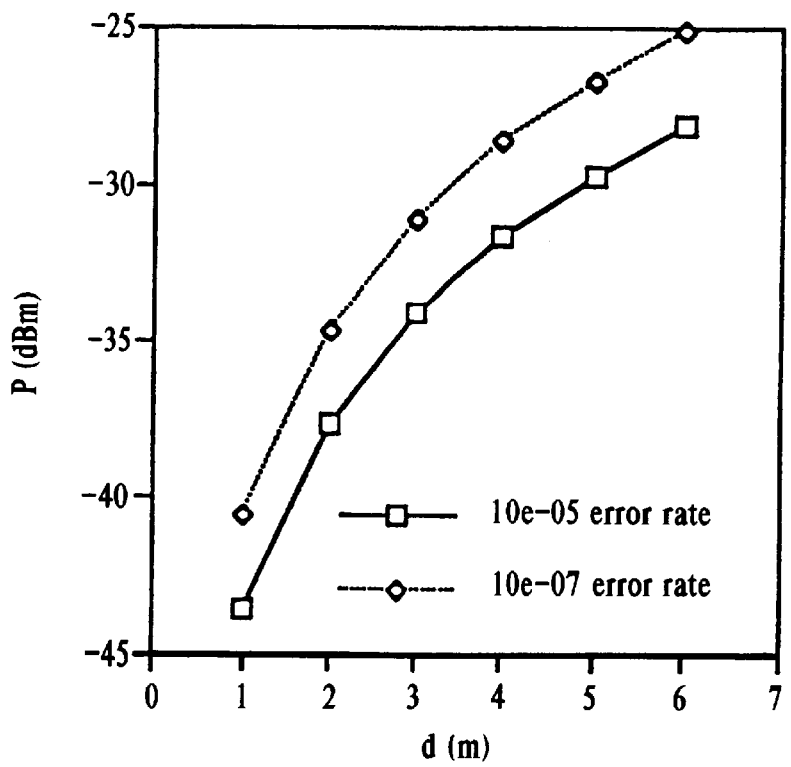
FIG. 6 is a graph depicting an exemplary relation between the required RF transmission power and the distance between the RF telemetry antennas of the implantable medical device and an external programmer at two data bit error rates.

Considering an implanted RF telemetry microstrip patch antenna operated at 350 MHz with antenna gain of −5 dB and the receiver antenna having a 3 dB gain, the power levels (milliWatts expressed in dB) required to cover a distance from 1–6 meters with bit error rates of $10^{-5}$ and $10^{-7}$ are shown in FIG. 6. At a distance of 2 meters and an error rate of $10^{-5}$, only about 2.0 microWatts of power is required. Assuming the telemetry transmitter 42 (FIG. 2) efficiency is conservatively estimated at 50%, and other efficiency margins including connector loss, receiver noise figure and other in-band electromagnetic noise source of 10 dB, 300 microWatts of power will be sufficient to transfer data at a distance of 2 meters and 2 milliWatts will provide uplink telemetry transmission over a distance of 5 meters.

Figure 9:
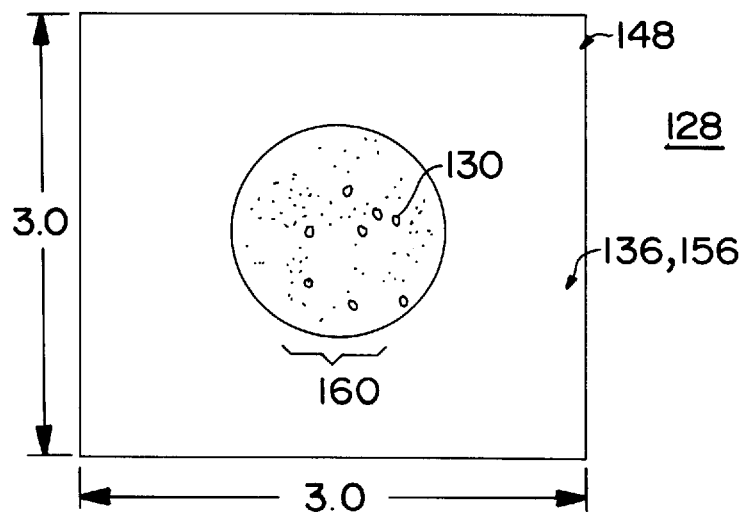
FIG. 9 is a top view of an experimental microstrip RF telemetry antenna breadboard.
Figure 10:
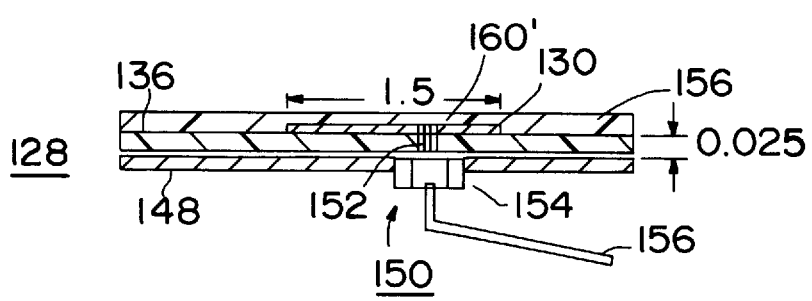
FIG. 10 is a side view of the experimental microstrip RF telemetry antenna breadboard of FIG. 9.
Figure 11:
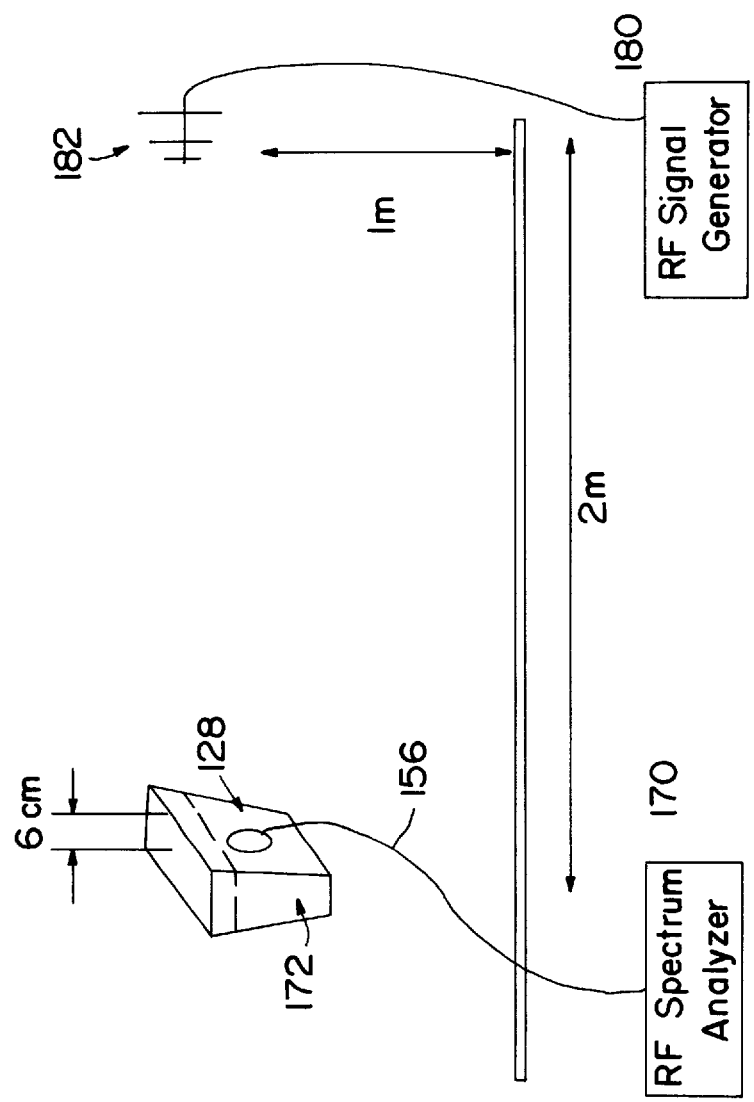
FIG. 11 is a schematic illustration of a test setup for testing the RF transmission characteristics of the experimental microstrip antenna breadboard in air and in a simulated human tissue mass.

FIGS. 9 and 10 depict top and side views (not necessarily drawn to scale) of a breadboard microstrip RF telemetry antenna 128 that is tested in the test setup of FIG. 11. In this breadboard, a circular, flat radiator patch layer 130 is formed of approximately 0.001 inch thick sheet of silver having a diameter of 1.5 inches that is fired upon the upper surface of a flat dielectric substrate layer 136. The dielectric substrate layer is a TransTech 3 inch square ceramic substrate that is 0.025 inches thick and has a dielectric constant of 78 and a loss tangent of 0.0245. A conductive, ground plane layer 148 of a 0.25 inch thick brass plate is adhered to the lower planar substrate surface by a conductive epoxy.

In this breadboard design, the ground plane layer 148 is also 3.0 inches square and provides a great enough area in comparison with the 1.5 inch area of the radiator patch layer to function as a microstrip RF antenna ground plane. As noted above, however, this 3.0×3.0 inch ground plane area is greater than that available across a major housing surface of most implantable medical devices. In order to compensate for the limited ground plane, one feature of the present invention provides that the layers of the RF telemetry antenna are formed in a housing recess as described below.

A feedthrough 150 including a feedthrough pin 152 and insulating ferrule 154 provide for an electrical connection with the radiator patch layer 130 and electrical isolation from the ground plane layer 148. The feedthrough pin 152 is extended through one of seven test attachment holes 160 formed at differing radii through the radiator patch layer 130 and is electrically connected with the lead wire 156 which is extended to a spectrum analyzer 170 in the test setup of FIG. 11.

In the tested breadboard design, the feedthrough 150 comprises an RF SMA male connector having a threaded flange surrounding the insulating ferrule 154 and electrically connected with the exposed surface of the ground plane layer 148. The female connector of a coaxial cable (not shown), is screwed onto the threaded flange thereby providing insulated electrical connections with the radiator patch layer 130 and the ground plane layer 148.

A radome is formed of an electrically insulating radome layer 156 that extends over the upper, exposed surfaces of the radiator patch layer 130 and the dielectric substrate layer 136. The radome layer 156 is preferably formed of a body compatible, insulative, low loss, low dielectric constant material, e.g. a layer of plastic, epoxy, glass, ceramic, etc.

The 1.5 inch diameter of the radiator patch layer 130 is chosen in light of the considerations of a practically sized microstrip antenna formed on or in the housing of an implantable medical device as described above. These materials, layer dimensions, the feedthrough characteristics and the dielectric constant of the dielectric substrate layer 136 provide for a resonant frequency of about 500 MHz in human tissue. The thickness of the dielectric substrate layer 136 affects the antenna bandwidth as described above. The radial offset of the chosen attachment hole 160' from the center of the circular radiator patch layer 130 affects the antenna input impedance to the transceiver it is attached to. The feed point impedance increases with radial offset of the feedthrough pin attachment point from the center of the radiator patch layer 130. In the breadboard RF telemetry antenna 128 of FIGS. 9 and 10, a radial offset of 0.375 inches from the center was selected in order to provide an impedance match of approximately 50 ohms.

In the test setup of FIG. 11, the breadboard RF telemetry antenna 128 is tested to determine antenna gain and return-loss when employed in a receiving mode, and receiving signals generated by a signal generator 180 and transmitted by a log-periodic, calibrated reference transmitting antenna 182. In FIG. 11, the breadboard RF telemetry antenna 128 is embedded 6 cm within in a phantom muscle tissue medium 172 simulating the RF transmission attenuation properties of in-vivo muscle tissue and constituting a mixture of gelling agent, water, salt and polyethylene particles. The radiator patch layer 130 is oriented to face outward of medium 172 and toward the transmitting antenna 182. The transmitting antenna 182 is placed on a stand about 1 meter above the floor of a large room and is connected to a calibrated RF signal generator 180 adjusted to generate 1 milliWatt (0 dBm) RF signals at frequencies sweeping between 505 and 525 MHz. The RF telemetry antenna 128 in medium 172 is located 2 meters away from the transmitting reference antenna 182. An RF spectrum analyzer sweeping through the same range is coupled to the lead 156.

The gain of the RF telemetry antenna is determined by taking readings of the received signal level in the spectrum analyzer 170 and subtracting it with the reference antenna gain, wave propagation path loss, wave loss in the phantom tissue antenna mismatch loss and cable loss. In addition to having a 5–8 dB better gain than lead or loop antennas tested under similar test conditions, the RF telemetry antenna 128 provides 150° or more, hemispheric, no-null coverage in space. Because of a null in coverage on the side of the grounding plane layer 148, it is advisable that the physician implant the implantable medical device having such an RF telemetry antenna of the present invention with the radiator patch layer 30, 130 facing outward toward the patient's skin as shown in FIG. 1.

The return-loss of the breadboard RF telemetry antenna 128 was measured in air with a network analyzer yielding a 26.7 dB return-loss at 516.8 MHz. A 5.85 dB return-loss at 516.8 MHz was attained in a further test with the RF telemetry antenna 128 embedded in the medium 172. The return-loss at the feedthrough pin attachment point was improved by covering the radiator patch layer 130 with a 0.038 inch thick plastic tape layer, which is a minimal thickness to achieve a return-loss better than 5.85 dB. This return-loss could be improved further by adjusting the radial offset of the feedthrough pin.

Figure 12:
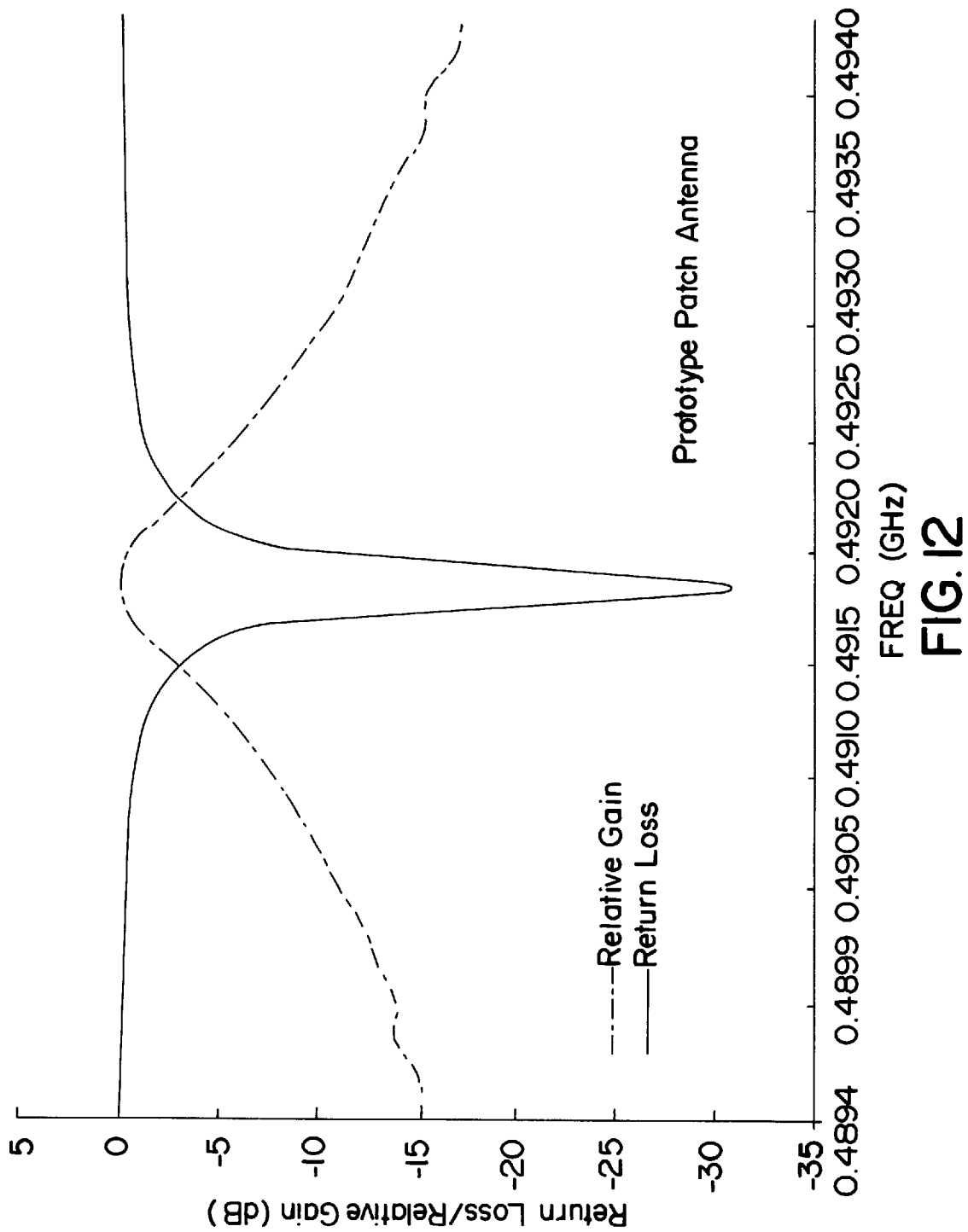
FIG. 12 is a graph depicting the relation between RF transmission frequency and predicted relative gain and return loss for the experimental microstrip antenna breadboard of FIGS. 9 and 10.

It is clear from the above that with a microstrip patch antenna design, a telemetry system can deliver data at very high rate, very low error rate over a relatively greater distance than conventional telemetry between an implanted medical device and an external programmer, with very low power consumption. This advantage is well suited to telemetry transmissions between implantable medical devices and external programmers or monitors. FIG. 12 depicts the simulated bandwidth performance of the breadboard RF telemetry antenna 128 and signifies that it possesses a high enough bandwidth to support high data rates.

Figure 13:
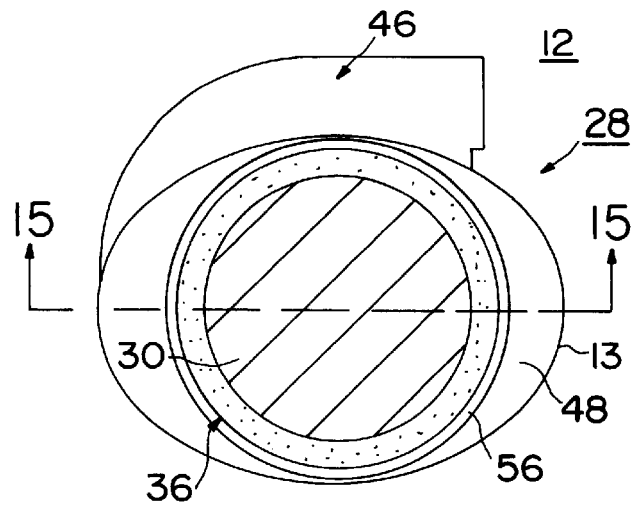
FIG. 13 is a schematic top view illustration of a first embodiment of an RF patch antenna formed on the exterior surface of a conductive housing of an implantable medical device that functions as the ground plane layer.
Figure 14:
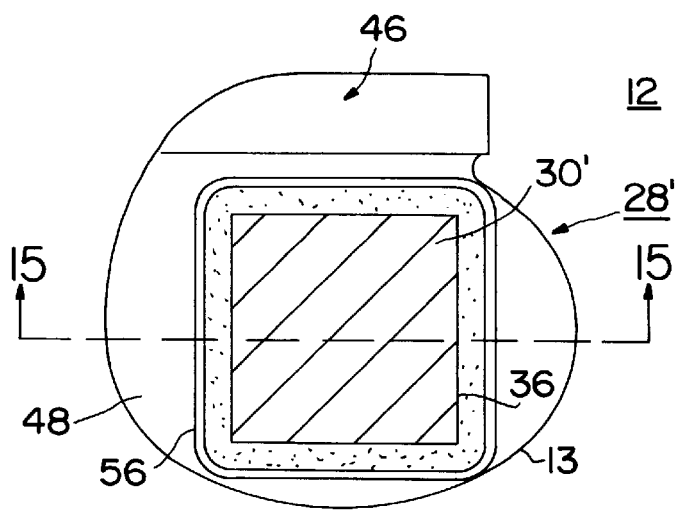
FIG. 14 is a schematic top view illustration of a second embodiment of an RF patch antenna formed on the exterior surface of a conductive housing of an implantable medical device functioning as the ground plane layer.
Figure 15:
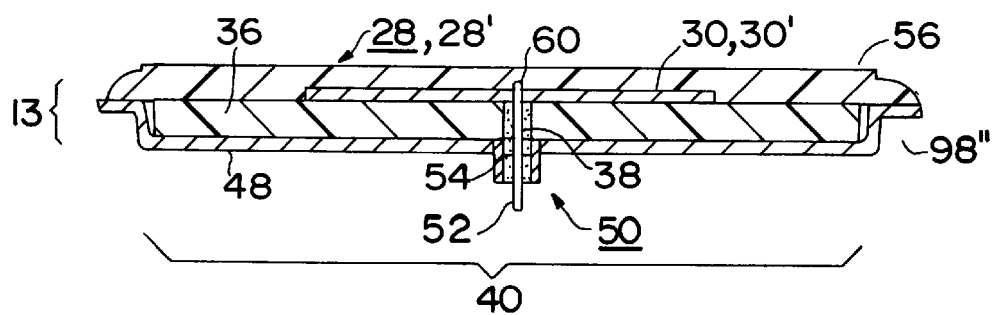
FIG. 15 is a schematic side cross-section view of the RF telemetry antenna taken along lines 15—15 of FIGS. 13 and 14.

FIGS. 13–15 depict first and second embodiments of RF telemetry antennas 28, 28' employing round and square (or rectangular) RF patch antenna plates or layers 30 and 30', respectively, formed over a dielectric substrate layer 36 and ground plane layer 48. The ground plane layer 48 is part of the conductive housing 13 of an IPG 12. The feedthrough pin 52 of feedthrough 50 extends through the ferrule 54 attached to the ground plane layer 48 and through the aligned hole 38 in the dielectric substrate layer 36 and the hole 60 in the radiator patch layer 30, 30'. The end of the feedthrough pin 52 is attached to the hole 60 by welding or the like. The actual location of the aligned holes 38 and 60 and the feedthrough 50 may be selected in the design phase to provide the best impedance match between the RF telemetry antenna 28, 28' and the associated IPG transceiver.

The areas of the radiator patch layer 30, 30' and the parallel ground plane layer 48 contribute to the RF frequency of the IPG RF telemetry antenna. Generally, it is necessary that the ground plane layer 48 area exceed that of the radiator patch layer 30, 30' Where it is necessary to size the radiator patch layer 30, 30' and the underlying dielectric layer 36 to cover most of the major flat exterior surface of the IPG housing 13, then performance of the IPG RF microstrip antenna is compromised. In this case, the exterior housing 13 is preferably recessed in a circular housing recess 40 having a recess depth to accommodate the thickness of the dielectric substrate layer 36 and a recess diameter or length and width to accommodate the radiator patch layer 30, 30'. The housing recess 40 of the ground plane layer 48 provides an outward ground plane extension layer 48" that is substantially co-planar with the radiator patch layer 30, 30' that effectively increases the area of the microstrip antenna ground plane 48.

In order to improve the IPG RF telemetry antenna performance within the body fluids and tissue, it is desirable to employ a dielectric radome layer over the otherwise exposed surface of the radiator patch layer 30, 30' that functions as a radome. Such an exemplary radome layer 56 is depicted in FIG. 15 and may be formed of the dielectric materials listed above. The radome layer 56 extends over the exterior surfaces of the radiator patch layer 30, 30', the dielectric layer 36 and the outwardly extending edge region 48" surrounding the housing recess 40 a suitable distance to the curved minor edge surface of the implantable medical device housing 13.

In the first and second embodiments, the conductive housing 13 and ground lane layer 48 are formed of a bio-compatible metal, e.g. titanium, in a manner well known in the art. When the implantable medical device is a unipolar IPG, an exposed surface portion of the housing 13 is used as an indifferent plate electrode for other electrical sensing and stimulation functions. The exposed indifferent electrode surface is preferably on the major, relatively flat, side of the IPG housing 13 opposite to the side where the RF telemetry antenna 28 is disposed. Disposing the RF telemetry antenna 28 to face toward the skin surface is advantageous for telemetry efficiency as noted above, and disposing the indifferent electrode surface inward is advantageous for both sensing electrical signals and electrical stimulation efficiency. As is known in the art, RF uplink and downlink telemetry transmissions can be synchronized with the operations of the implantable medical device to avoid times when the device operations involve electrical stimulation and/or sensing, although it may not be necessary to do so in the practice of the present invention.

Figure 16:
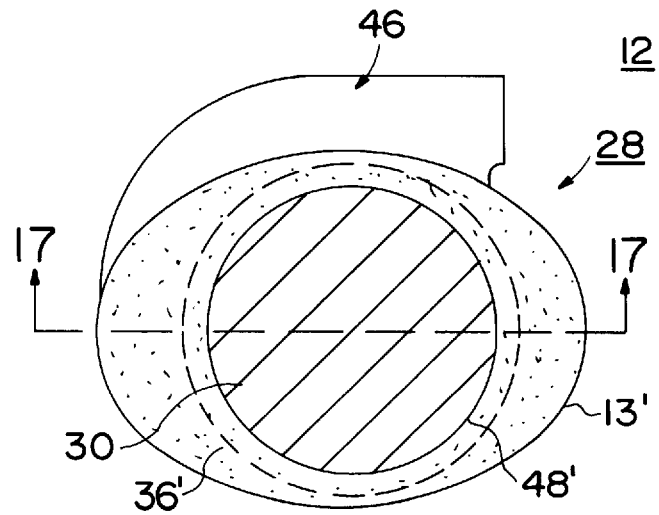
FIG. 16 is a schematic top view illustration of a third embodiment of an RF telemetry antenna formed on the exterior surface of a dielectric housing of an implantable medical device having a ground plane layer formed inside the housing.
Figure 17:
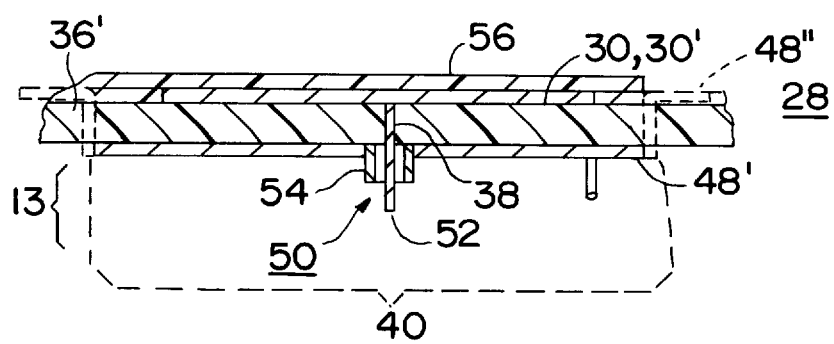
FIG. 17 is a schematic side cross-section view of the RF telemetry antenna taken along lines 17—17 of FIG. 16.

FIGS. 16 and 17 depict a third embodiment of an RF telemetry antenna 28 with the radiator patch layer 30, 30' formed on the exterior surface of a dielectric, ceramic, housing 13' of an IPG 12 and having a ground plane layer 48' formed as a conductive layer on the interior surface of the IPG housing 13'. Therefore, in this embodiment, the dielectric IPG housing 13' of the type described in the above-incorporated '345 patent, for example, constitutes and provides the dielectric substrate layer 36' disposed between the ground plane layer 48' and the radiator patch layer 30, 30'. It will be understood that the ground plane layer 48' is insulated electrically from interior circuit components within the IPG housing. This embodiment also illustrates an alternative form of the feedthrough pin 52 which fills the dielectric layer hole 38 and is abutted against the interior surface of the radiator patch layer 30, 30'. In this case, the radiator patch layer 30, 30' is optimally formed by thick or thin film deposition or adherence of a metal layer over the exterior surface of the dielectric IPG housing. The radiator patch layer 30, 30' is preferably formed to extend into the hole 38 to the extent necessary to fill it and make secure electrical contact with the end of the feedthrough pin 52.

In this embodiment, if the ground plane layer 48' is not large enough in area relative to the radiator patch layer 35' then it may be necessary to form a rim or ring shaped, conductive, ground plane extension layer 48' (shown in broken lines) extending around and spaced apart from the periphery of the radiator patch layer 30, 30'. The ground plane extension layer 48" is electrically connected to the ground plane layer 48' at least at one electrical connection, e.g., one or more plated through hole through the dielectric layer 36'. This electrical connection may alternatively be effected by providing the ground plane layer 48 as a single, dish shaped, layer that is fabricated with the major side of the medical device non-conductive housing 13' to mimic the arrangement of the embodiment of FIGS. 13–15. In this variation, the dielectric layer 36' is formed as a separate layer within the housing recess created thereby in the manner described above with respect to FIGS. 13–15.

In either variation, a radome layer 56 is also preferably formed overlying the exterior surfaces of the radiator patch layer 30, 30', the dielectric layer 36', and at least a portion of the ring shaped ground plane extension layer 48" (if present) employing one of the above-identified materials.

Figure 18:
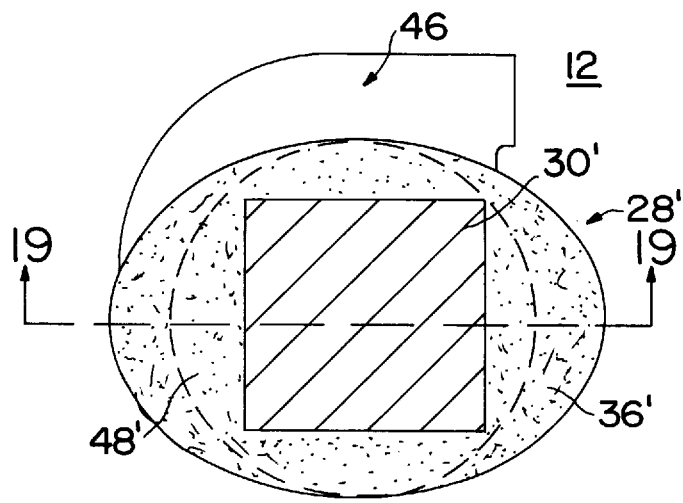
FIG. 18 is a schematic top view illustration of a fourth embodiment of an RF telemetry antenna having a radiator patch layer formed within the surface of an insulative, dielectric housing of an implantable medical device.
Figure 19:
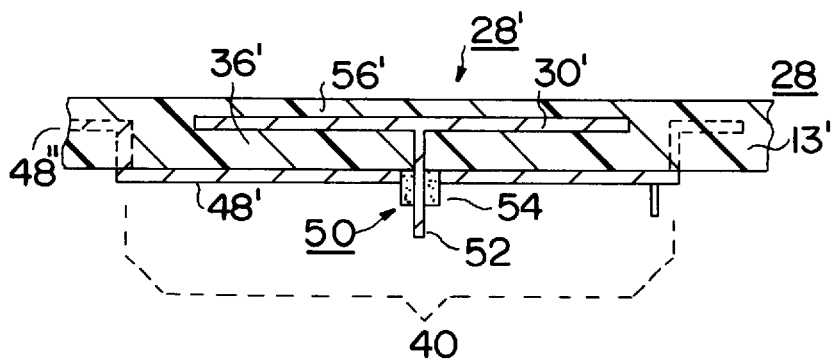
FIG. 19 is a schematic side cross-section view of the RF telemetry antenna taken along lines 19—19 of FIG. 18.

FIGS. 18 and 19 depict a fourth embodiment of an RF telemetry antenna 28 having the radiator patch layer 30, 30' formed as a layer within the insulative dielectric IPG housing 13'. In this embodiment, the outer layer of the non-conductive housing 13 functions as the radome layer 56'. The ground plane layer 48' is formed as a conductive layer on the interior surface or within the IPG housing 13' in the manner described above. The ground plane extension layer 48" (shown in broken lines) is also formed as a layer that is substantially co-planar with the radiator patch layer 30, 30' within the insulative dielectric IPG housing 13' and is electrically connected with the ground plane layer 48 as described above.

In each of the preferred embodiments, the radiator patch layer is preferably formed of a stable, bio-compatible, conductive layer that is applied as a thin plate or thin film deposition over the exterior surface of the dielectric layer. The radiator patch layer may be formed of a noble metal, e.g. gold, platinum, niobium, or an alloy thereof.

Thus, the microstrip RF telemetry antenna of the present invention is formed of a conductive, radiator patch layer that is laminated upon one surface of a relatively uniform thickness dielectric substrate layer overlying a conductive ground plane and electrically isolated therefrom. The patch antenna layer is coupled to the transceiver circuitry within the hermetically sealed housing of the IPG by a feedthrough extending through the implantable medical device housing and the dielectric layer. Preferably, the implantable medical device housing is conductive and forms the ground plane, and the dielectric layer and patch layer are formed on its exterior surface. However, the IPG housing may be non-conductive and form the dielectric layer separating the patch electrode from the ground plane. The dielectric layer and patch antenna layer are conformal with any curvature of the implantable medical device housing, particularly as the edges of the major planar surfaces thereof are approached.

The external RF telemetry antenna for the external programmer may be configured and constructed in a similar manner as described above. However, since the available surface area is relatively unlimited, it may not be necessary to employ a recessed construction of the ground plane layer as depicted in FIG. 15 and described above. Moreover, the materials employed for the microstrip antenna layers and the thickness, area, etc., of each layer may differ from those employed in the IPG microstrip antenna fabrications of the present invention as illustrated in the above-described, exemplary embodiments.

The preceding specific embodiments are illustrative of the practice of the invention. It is to be understood, therefore, that other expedients known to those of skill in the art or disclosed herein may be employed without departing from the invention or the scope of the appended claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

It is therefore to be understood, that within the scope of the appended claims, the invention may be practiced otherwise than as specifically described without actually departing from the spirit and scope of the present invention.

What is claimed is:

1. A telemetry system for communications between an external programmer and an implantable medical device, comprising:

the external programmer comprising an external telemetry antenna and an external transceiver for receiving uplink telemetry transmissions and transmitting downlink telemetry transmission through the external telemetry antenna;

the implantable medical device comprising an implantable medical device housing, an implantable telemetry antenna and an implantable transceiver for receiving downlink transmissions and for transmitting uplink telemetry transmission through the implantable telemetry antenna, the implantable medical device housing being formed of a conductive metal and having an exterior housing surface and an interior housing surface;

the implantable medical device housing being formed with a housing recess extending inwardly from the exterior housing surface to a predetermined housing recess depth in the predetermined substrate area of the exterior housing surface for receiving the dielectric substrate therein;

wherein the implantable telemetry antenna is a conformal microstrip antenna formed as part of the implantable medical device housing, the microstrip antenna having electrically conductive ground plane and radiator patch layers separated by a dielectric substrate, layer the conductive radiator patch layer having a predetermined thickness and predetermined radiator patch layer dimensions, the patch layer being formed upon one side of the dielectric substrate layer.

2. A telemetry system for communication between an external programmer and an implantable medical device, wherein:

the external programmer comprises an external telemetry antenna and an external transceiver from receiving uplink telemetry transmissions and transmitting downlink telemetry transmissions through the external telemetry antenna;

the implantable medical device comprises an implantable medical device housing, an implantable telemetry antenna and an implantable transceiver for receiving downlink telemetry transmissions and for transmitting uplink telemetry transmission through the implantable telemetry antenna, the implantable medical device housing being formed of a conductive metal and having an exterior housing surface and an interior housing surface, the implantable medical device housing further being formed with a housing recess extending inwardly from the exterior housing surface to a predetermined housing recess depth in the predetermined substrate area of the exterior housing surface for receiving the dielectric substrate therein, the implantable medical device housing being formed as a conductive metal layer adhering to the interior housing surface;

the implantable telemetry antenna is a conformal microstrip antenna formed as part of the implantable medical device housing, the microstrip antenna having electrically conductive ground plane and radiator patch layers separated by a dielectric substrate layer the conductive radiator patch layer having a predetermined thickness and predetermined radiator patch layer dimensions, the patch layer being formed upon one side of the dielectric substrate layer;

the conductive ground plane layer is at least a portion of the conductive metal housing and has predetermined ground plane dimensions such that the conductive ground plane layer extends substantially in parallel to and at least coextensively with the conductive radiator patch layer, and the dielectric substrate is formed over a predetermined substrate area of the exterior housing surface, the dielectric substrate having an exposed exterior substrate surface, and the conductive radiator patch is formed over at least a portion of the extension substrate surface.

3. The telemetry system of claim 1 further comprising a diadem layer of dielectric material formed over the conductive radiator patch layer.

4. The telemetry system of claim 1, wherein the implantable medical device housing is formed of a non-conductive dielectric substrate layer having an exterior housing surface and an interior housing surface;

the conductive ground plane layer is formed as a conductive metal layer adhering to the interior housing surface; and the conductive radiator patch layer is formed between the exterior and interior housing surfaces to extend parallel to the ground plane layer and to be separated therefrom by an intermediate dielectric substrate layer of the medical device housing.

5. The telemetry system of any of preceding claims 1, 2 or 4, wherein the transceiver is disposed within the implantable medical device housing and further comprises feedthrough means extending through the conductive ground plane layer and the dielectric substrate layer to the radiator patch layer for electrically connecting the implantable transceiver within the implantable medical device housing with the radiator patch layer.

6. The telemetry system of any of preceding claims 1, 2 or 4 further comprising means for forming a ground plane layer extension in the same plane as, and surrounding the periphery of, the patch radiator layer.

7. An implantable medical device, comprising:

an implantable telemetry antenna;

an implantable medical device housing; and a transceiver coupled to the implantable telemetry antenna for communications between an external medical device and the implantable medical device, wherein the implantable telemetry antenna is conformal microstrip antenna formed as part of the implantable medical device housing, the microstrip antenna having electrically conductive ground plane and radiator patch layers separated by a dielectric substrate layer, the implantable medical device housing is formed of a non-conductive dielectric substrate layer having an exterior housing surface and an interior housing surface;

the conductive ground plane layer is formed as a conductive metal layer adhering to the interior housing surface, and the conductive radiator patch layer is formed over at least a portion of the exterior housing surface.

8. The telemetry antenna of claim 7, wherein the conductive radiator patch layer has predetermined radiator patch layer dimensions and is formed upon one side of the dielectric substrate layer, the implantable medical device housing is formed of a conductive metal and has an exterior housing surface and an interior housing surface;

the conductive ground plane layer is at least a portion of the conductive metal housing and has predetermined ground plane dimensions such that the conductive ground plane layer extends substantially in parallel to and at least coextensively with the conductive radiator patch layer;

the dielectric substrate is formed over a predetermined substrate area of the exterior housing surface, the dielectric substrate having an exposed exterior substrate surface;

the conductive radiator patch layer is formed over at least a portion of the exterior substrate surface, and the implantable medical device housing is formed with a housing recess extending inwardly from the exterior housing surface to a predetermined housing recess depth in the predetermined substrate area of the exterior housing surface for receiving the dielectric substrate therein.

9. The telemetry antenna of any of preceding claims 7 or 8, further comprising a radome layer of dielectric material formed over the conductive radiator patch layer.

10. The telemetry antenna of claim 7, wherein the implantable medical device housing is formed of a non-conductive dielectric substrate layer having an exterior housing surface and an interior housing surface;

the conductive ground plane layer is formed as a conductive metal layer adhering to the interior housing surface; and the conductive radiator patch layer is formed between the exterior and interior housing surfaces to extend parallel to the ground plane layer and to be separated therefrom by an intermediate dielectric substrate layer of the medical device housing.

11. The telemetry antenna of any of preceding claims 7, 8 or 10, wherein the transceiver is disposed within the implantable medical device housing and further comprises feedthrough means extending through the conductive ground plane layer and the dielectric substrate layer to the radiator patch layer for electrically connecting the implantable transceiver within the implantable medical device housing with the radiator patch layer.

12. The telemetry antenna of any of preceding claims 7, 8 or 10 further comprising the step of forming a ground plane layer extension in the same plane as, and surrounding the periphery of, the patch radiator layer.

13. A method of forming an implantable RF telemetry antenna as part of the housing of an implantable medical device for telemetry between an external medical device and the implantable medical device, comprising the steps of:

forming an implantable medical device housing having exterior housing surface and an interior housing surface for receiving components of the implantable medical device therein;

disposing a transceiver for receiving downlink telemetry transmissions and for transmitting uplink telemetry transmissions through the implantable RF telemetry antenna within the implantable medical device housing; and forming a conformal microstrip antenna as part of the implantable medical device housing, the microstrip antenna having a conductive ground plane layer and a conductive radiator patch layer separated by a dielectric substrate layer.

14. The method of claim 13, wherein the microstrip antenna forming step further comprises forming the dielectric substrate layer with a predetermined substrate layer thickness and an interior substrate surface and an exterior substrate surface; and forming the electrically conductive radiator patch layer on the exterior substrate surface to have predetermined radiator patch layer dimensions.

15. The method of claim 14, further comprising the step of forming the conductive ground plane layer on the interior substrate surface to have predetermined ground plane dimensions such that the conductive ground plane layer extends substantially in parallel to and at least coextensively with the conductive radiator patch layer.

16. The method of claim 13, wherein the step of forming an implantable medical device housing further comprises forming the implantable medical device housing of a conductive metal such that the conductive ground plane layer is at least a portion of the conductive metal housing; and the step of forming the microstrip antenna further comprises the steps of:

forming the dielectric substrate layer on at least a portion of the exterior housing surface to have a predetermined substrate layer thickness and an interior substrate surface and an exterior substrate surface; and forming the electrically conductive radiator patch layer on at least a portion of the exterior substrate surface.

17. The method of claim 13, wherein the step of forming an implantable medical device housing further comprises the steps of:

forming the implantable medical device housing of a conductive metal such that the conductive ground plane layer is at least a portion of the conductive metal housing; and forming a housing recess extending inwardly from the exterior housing surface to a predetermined housing recess depth in a predetermined substrate area of the exterior housing surface; and the step of forming the microstrip antenna further comprises the steps of:

forming the dielectric substrate layer within the housing recess to have a relatively constant thickness and interior and exterior substrate surfaces; and forming the conductive radiator patch layer on at least a portion of the exterior substrate surface.

18. The method of claim 13, wherein the step of forming an implantable medical device housing comprises forming the implantable medical device housing of a non-conductive dielectric material; and the step of forming the microstrip antenna further comprises the steps of:

forming the conductive radiator patch layer on the exterior housing surface to have predetermined radiator patch layer dimensions and an exposed radiator patch layer surface; and forming the conductive ground plane layer as a conductive metal layer adhering to the interior housing surface, wherein the implantable medical device housing functions as the dielectric substrate layer with a relatively constant thickness.

19. The method of any one of the preceding claims 13–18 further comprising the step of forming a radome layer of dielectric material over the exposed radiator patch layer surface.

20. The method of claim 13, wherein the step of forming an implantable medical device housing comprises forming the implantable medical device housing of a non-conductive dielectric material; and the step of forming the microstrip antenna further comprises the steps of:

forming the electrically conductive radiator patch layer between the exterior and interior housing surfaces; and forming the conductive ground plane layer as a conductive metal layer adhering to the interior housing surface such that an intermediate dielectric substrate layer of the implantable medical device housing functions as the dielectric substrate layer.

21. The method of any of the preceding claims 13–18 or 20 further comprising the step of extending feedthrough means through the conductive ground plane layer and the dielectric substrate layer to electrically connect the transceiver within the implantable medical device housing with the conductive radiator patch layer.

22. The method of any of the preceding claims 13–18 or 20 further comprising the step of forming a ground plane layer extension in the same plane as, and surrounding the periphery of, the patch radiator layer.

\* \* \* \* \*